United States Patent [19]
Barrie et al.

[11] Patent Number: 5,618,807
[45] Date of Patent: Apr. 8, 1997

[54] METHOD FOR PREPARING 17-SUBSTITUTED STEROIDS USEFUL IN CANCER TREATMENT

[75] Inventors: Susan E. Barrie, Kent; Michael Jarman, London; Gerard A. Potter, Cheshire; Ian R. Hardcastle, Sutton, all of Great Britain

[73] Assignee: British Technology Group Limited, London, England

[21] Appl. No.: 392,178

[22] Filed: Feb. 22, 1995

Related U.S. Application Data

[62] Division of Ser. No. 315,882, which is a continuation-in-part of PCT/GB93/00531, Mar. 15, 1993.

[30] Foreign Application Priority Data

Mar. 31, 1992 [GB] United Kingdom ............... 9207057
Nov. 27, 1992 [GB] United Kingdom ............... 9224880
Sep. 30, 1993 [GB] United Kingdom ............... 9320132
Jul. 14, 1994 [GB] United Kingdom ............... 9414192

[51] Int. Cl.$^6$ .............................. A61K 31/58; C07J 43/00
[52] U.S. Cl. ..................................... 514/176; 540/95
[58] Field of Search ......................... 540/92, 95; 514/176

[56] References Cited

FOREIGN PATENT DOCUMENTS 288053  10/1988  European Pat. Off. .
413270   2/1991  European Pat. Off. .

OTHER PUBLICATIONS

Wicha et al, Bulletin of the Polish Acad of Sciences, chemistry 32 pp. 75–83 (1984).
Wicha et al Heterocycles vol. 16 pp. 521–524 (1981).
Wicha et al, Heterocycles vol. 20 pp. 231–234 (1983).
J. Wicha et al. "Cardiotonic steroids. Part 8. Synthesis of 17.beta . . . " Bulletin of the Polish Acad. of Sciences, Chemistry vol. 33 No. 1–2, 1985, pp. 19–27.
J. Wicha et al. "Cardiotonic steriods. Part 7. Synthesis of 17.beta . . . " Bulletin of the Polish Acad. of Sciences. Chemistry, vol. 32 No. 1–2, 1984, pp. 75–83.
J. Wicha et al. "Synthesis of 17.beta–pyridyl . . . " Heterocycles, vol. 16 No. 4, 1981, pp. 521–524.
J. Wicha et al. "Synthesis and Molecular biological activity of the pyridine . . . " Heterocycles. vol. 20 No. 2, 1983, pp. 231–234.
G. A., Potter et al. "Discovery of Highly potent and selective enzyme . . . " Poster presented at the SmithKline Beecham Research Symp., Robinson College, Cambridge, England, 25–26 Mar. 1993.

S. E. Barrie et al. "Highly potent inhibitors of human cytochrome . . . " Poster presented at the British Association for Cancer Research meeting in Sheffield, England, 28–31 Mar. 1993.

G. A. Potter et al. "Highly potent inhibitors of human cytrochrome P–450 . . . " Poster presented at the third Drug Discovery & Development Symp., San Diego, CA, USA, 22–24 Jul. 1993.

B. Schweder et al. "Synthesis des . . . " J. Prakt. Chem. 335, 201–204 (1993).

D. H. R. Barton et al. "An improved preparation of vinyl iodides . . . " Tetrahedron letters, 24, 1605–1608 (1983).

D. H. R. Barton et al. "Studies on the oxidation of hydrazones with iodide . . . ", Tetrahedron 44, 147–162 (1988).

M. J. Shiao. "New synthesis of azabufalin from C–17 steroidal ketones", J. Org. Chem. 47, 5189–5191 (1982).

Primary Examiner—Mukund J. Shah
Assistant Examiner—Anthony Bottino
Attorney, Agent, or Firm—Nixon & Vanderhye

[57] ABSTRACT

Compounds of the general formula (1)

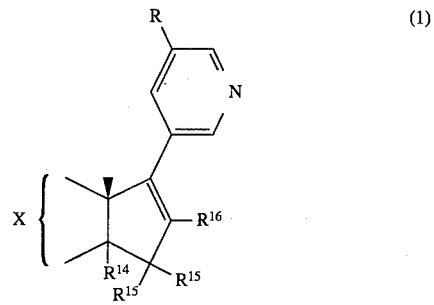

(1)

wherein X represents the residue of the A, B and C rings of a asteroid, R represents a hydrogen atom or an alkyl group of 1 to 4 carbon atoms, $R^{14}$ represents a hydrogen atom and $R^{15}$ represents a hydrogen atom or an alkyl or alkoxy group of 1–4 carbon atoms, or a hydroxy or alkylcarbonyloxy group of 2 to 5 carbon atoms or $R^{14}$ and $R^{15}$ together represent a double bond, and $R^{16}$ represents a hydrogen atom or an alkyl group of 1 to 4 carbon atoms, in the form of the free bases or pharmaceutically acceptable acid addition salts, are used for treatment of androgen-dependent disorders, especially prostatic cancer, and also oestrogen-dependent disorders such as breast cancer.

9 Claims, No Drawings

METHOD FOR PREPARING 17-SUBSTITUTED STEROIDS USEFUL IN CANCER TREATMENT

This is a Rule 60 Divisional of application Ser. No. 08/315,882, filed Sep. 30, 1994.

This specification is a continuation-in-part of PCT Application PCT/GB93/00531, filed Mar. 15, 1993 and which designated the United States of America.

BACKGROUND OF THE INVENTION

1. Field of the Invention

This invention relates to 17-substituted steroids and their use in the treatment of androgen-dependent and oestrogen-dependent disorders, especially prostatic cancer and breast cancer respectively.

2. Description of the Related Art

The 17α-hydroxylase/$C_{17-20}$ lyase enzyme complex (hereinafter "hydroxylase/lyase") is known to be essential for the biosynthesis of androgens and oestrogens. In the treatment of androgen-dependent disorders, especially prostatic cancer, there is a need for strong inhibitors of hydroxylase/lyase. Certain anti-androgenic steroids are well known, for example Cyproterone acetate (17α-acetoxy-6-chloro-1α, 2α-methylene-4,6-pregnadiene-3,20-dione). Many other steroids have been tested as hydroxylase/lyase inhibitors. See, for example, PCT Specification WO 92/00992 (Schering AG) which describes anti-androgenic steroids having a pyrazole or triazole ring fused to the A ring at the 2,3-position, or European Specifications EP-A 288053 and EP-A 413270 (Merrell Dow) which propose 17β-cyclopropylamino androst-5-en-3β-ol or -4-en-3-one and their derivatives.

SUMMARY OF THE INVENTION

It has now surprisingly been found that steroids lacking a $C_{20}$ side chain and having a 17-(3-pyridyl) ring in its place, together with a 16,17-double bond, are powerful hydroxylase/lyase inhibitors, useful for the above-stated purposes.

According to the invention, there are provided compounds of the general formula

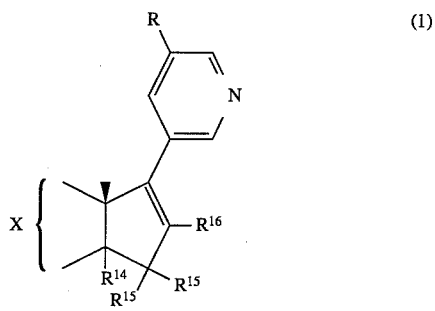

(1)

wherein X represents the residue of the A, B and C rings of a steroid, R represents a hydrogen atom or an alkyl group of 1–4 carbon atoms, $R^{14}$ represents a hydrogen atom, a halogen atom or an alkyl group of 1 to 4 carbon atoms and each of the $R^{15}$ substituents independently represents a hydrogen atom or an alkyl or alkoxy group of 1–4 carbon atoms, a hydroxy group or an alkylcarbonyloxy group of 2 to 5 carbon atoms or together represent an oxo or methylene group or $R^{14}$ and one of the $R^{15}$ groups together represent a double bond and the other $R^{15}$ group represents a hydrogen atom or an alkyl group of 1 to 4 carbon atoms, and $R^{16}$ represents a hydrogen atom, halogen atom, or an alkyl group of 1 to 4 carbon atoms, in the form of the free bases or pharmaceutically acceptable acid addition salts.

The term "steroid" herein includes any compound having the steroidal B and C rings, but in which all or part of the A ring is missing e.g. ring not closed (lacking the 2-or 3-position C-atom or both) or takes the form of a cyclopentane ring. It also includes azasteroids having a ring nitrogen atom in place of a ring carbon atom, especially in the A-ring such as in 4-azasteroids.

In general, the compounds of formula (1) are new and such compounds per se are included in the invention. However, certain of them have been disclosed as intermediates in the synthesis of certain steroids having a 3-pyridyl or 3-pyridonyl group in the 17β-position, see J. Wicha and M. Masnyk, Bulletin of the Polish Academy of Sciences: Chemistry 33 (1–2), 19–27 and 29–37 (1985). The first of these papers says that a 17β-side chain of the form —C=C—C=O or —C=C—C=N favours cardiotonic properties and describes the synthesis of 17β(3-pyridyl)-14β-androst-4-ene-3β, 14-diol, while the second uses this compound to prepare 17β3-pyrid-2(1H)onyl]-14β-androst-4-ene-3β, 14-diol. Those final compounds differ from those of the present invention by having a saturated D-ring and the paper contains no test results. Insofar as certain compounds within formula (1) are known as intermediates in these syntheses, the invention extends to the compounds only for use in therapy. These are 3 β-acetoxy- 17-( 3-pyridyl)androsta-5, 14,16-triene and 3β, 15β- and 3β,15β-diacetoxy-17-(3-pyridyl)androsta-5,16-diene. See also J Wicha. et. al., Heterocycles 20, 231–234 (1983) which is a preliminary communication of the first of the above two papers.

J. Wicha et. al., Bulletin of the Polish Academy of Sciences, Chemistry 32 (1–2), 75–83 (1984) have also described the preparation of 3β-methoxy-17β-(3-pyridyl)androstane and pyridone analogues thereof via the intermediate 3β-methoxy-17-(3-pyridyl)-5α,-androst-16-ene. Accordingly, the invention extends to the latter compound only for use in therapy. A preliminary communication of this paper, by J. Wicha and M. Masynk, appeared in Heterocycles 16, 521–524 (1981).

The invention also includes pharmaceutical compositions comprising a compound of formula (1) in association with a pharmaceutically acceptable diluent or carrier. The terminology "pharmaceutical compositions" implies that injectible formulations are sterile and pyrogen-free and thereby excludes any compositions comprising the compound of formula (1) and a non-sterile organic solvent, such as may be encountered in the context of the final stages of preparing these above-mentioned compounds of formula (1) which have been described in the literature but without any therapeutic use being mentioned.

DESCRIPTION OF THE PREFERRED EMBODIMENTS

In the compounds of the invention the essential structural features comprise all of:
a 3-pyridyl ring in the 17-position
a ring double bond in the 16, 17-position of the D-ring
the 18-position methyl group It is critical that the pyridine nitrogen atom be in the 3-position, not the 2- or 4-position. It is also critical that the pyridine ring be joined directly to the 17-carbon atom. This criticality is demonstrated by tests of inhibiting activity against hydroxylase and lyase (Table 1). The concentration of test compound required to achieve 50% inhibition of the enzyme is far greater for the 2-pyridyl, 4-pyridyl and 2-pyridylmethyl compounds tested than for the 3-pyridyl. The methods of determination were as described in the Examples hereinafter.

TABLE 1

Effect of variations in the 17-substitutent on inhibition of hydroxylase and lyase demonstrating the criticality of the 17-substituent in this invention

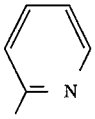

| $R^{17}$ | Type | IC$_{50}$ (µM) Lyase | IC$_{50}$ (µM) Hydroylase |
|---|---|---|---|
| 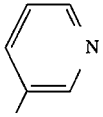 | 2-Pyridyl (for comparison) | 0.13 | 0.32 |
| 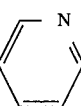 | 3-pyridyl (present invention) | 0.003 | 0.004 |
| 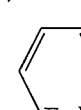 | 4-pyridyl (for comparison) | 2.0 | 5.0 |
| 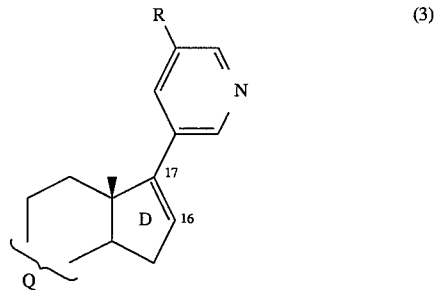 | 2-picolyl (for comparison) | >10 | >10 |

Note:
all the compounds of formula (2) tested were poor inhibitors of aromatase: IC$_{50}$ > 20 µM.

Our modelling of the geometry of the putative transition state of the lyase component of the hydroxylase-lyase enzyme complex, in the putative mechanism of action of the lyase component, suggests that the 16, 17-double bond is essential to allow the 3-pyridine ring to adopt the orientation required for co-ordination to the haem group of the hydroxylase-lyase complex.

Elsewhere, the D-ring can have any other simple substituent. Certain simple substituents are defined in connection with the preferred general formula (1), but it will be appreciated that others could be substituted for those of formula (1). In the compounds of formula (1), $R^{15}$ is preferably hydrogen or alkyl of 1 to 3 carbon atoms, $R^{16}$ hydrogen, alkyl of 1 to 3 carbon atoms, fluorine, chlorine, bromine or iodine, and R hydrogen or methyl, in the 5-position of the pyridine ring.

The remainder of the molecule, designated "X" in formula (1), can be of any kind conventional in steroid chemistry or have any other feature known in steroids having anti-androgenic activity, for example the pyrazole or triazole ring, fused to the A ring at the 2- and 3- positions, disclosed in the above-cited Specification WO 92/00992, or oxazole ring fused in the same positions.

By way of example, X can represent the residue of androstan-3α- or 3β-ol,
androst-5-en-3α- or 3β-ol,
androst-4-en-3-one,
androst-2-ene,
androst-4-ene,
androst-5-ene,
androsha-5,7-dien-3α or 3β-ol,
androsha-1,4-dien-3-one.
androsha-3,5-diene,
estra- 1,3,5[10]-triene,
estra-1,3,5[10]-trien-3-ol,
5α-androstan-3-one,
androst-4-ene-3,11 -dione,
6-fluoroandrost4-ene-3-one or
androstan-4-ene-3,6-dione
each of which, where structurally permissible, can be further derivatised in one or more of the following ways:
to form 3-esters, especially 3-alkanoates, and -benzoates,
to have one or more carbon to carbon ring double bonds in any of the 5,6-, 6,7- 7,8-, 9,11- and 11,12-positions
as 3-oximes
as 3-methylenes
as 3-carboxylates
as 3-nitriles
as 3-nitros
as 3-desoxy derivatives
to have one or more hydroxy, halo, $C_{1-4}$-alkyl, trifluoromethyl, $C_{1-4}$-alkoxy, $C_{1-4}$-alkanoyloxy, benzoyloxy, oxo, methylene or alkenyl substituents in the A, B or C-ring to be 19-nor.

Preferred $C_{1-4}$-alkyl and alkoxy groups are methyl and ethoxy.

Preferred $C_{1-4}$-alkanoyloxy groups are acetoxy and propanoyloxy.

Preferred halo groups are fluoro, bromo and chloro and the preferred substitution position is the 6-position.

The substituents include, for instance, 2-fluoro, 4-fluoro, 6-fluoro, 9-fluoro, 3-trifluoromethyl, 6-methyl, 7-methyl, 6-oxo, 7-oxo, 11-oxo, 6-methylene, 11-methylene, 4-hydroxy, 7-hydroxy, 11-hydroxy or 12-hydroxy, each in any appropriate epimeric form, and, subject to structural compatibility (well known in general steroid chemistry), in any combination of two or more such groups.

Compounds which are likely to be unstable are considered excluded from consideration. Such compounds will be evident to steroid chemists. Compounds having esoteric substituents likely to interfere with the stereochemical alignment of the steroid molecule with the enzymes to be inhibited, by virtue of steric or electronic distribution effects, are to be avoided. For example, a 2,3,5,6-tetrafluoro-4-trifluoromethylphenoxy substituent in the 3-position is not recommended. Androst-5βen-3β-ol having such an ether substituent in place of the 3β-hydroxy group has been shown to be a very poor inhibitor for lyase and hydroxylase.

The currently preferred compounds of formula (1) include those which are saturated and unsubstituted at the 11- and 12-positions and which therefore are of the general formula (3):

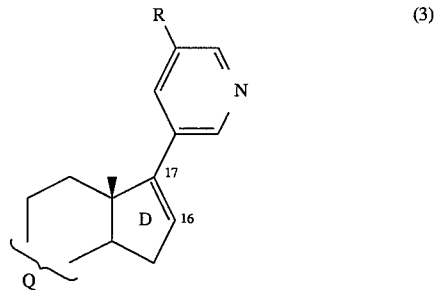

wherein Q represents the residue of A, B and C rings of a steroid, and R is a hydrogen atom or an alkyl group of 1–4 carbon atoms.

However, 11- and/or 12-substituted compounds are also active. Particularly preferred are 11-oxo and 11β-hydroxy derivatives of compounds of formula (3).

Specifically preferred compounds of be invention comprise
17-(3-pyridyl)androsta-5,16-dien-3β-ol,
17-(3-pyridyl)androsta-3,5,16-triene,
17-(3-pyridyl)androsta-4,16-dien-3-one,
17-(3-pyridyl)estra-1,3,5[10],16-tetraen-3-ol,
17-(3-pyridyl)-5α-androst- 16-en-3α-ol and their acid addition salts and 3-esters.

Other notable compounds of the invention comprise
17-(3-pyridyl)-5=-androst- 16-en-3-one,
17-(3-pyridyl)-androsta4,16-diene-3,11-dione,
17-(3-pyridyl)-androsm-3,5,16-trien-3-ol,
6α- and 6β-fluoro-17-(3-pyridyl)androsta-4,16-dien-3-one
17-(3-pyridyl)androsta-4, 16-dien-3,6-dione,
17-[3-(5-methyl pyridyl)]androsta-5,16 dien-3β-ol
3α-trifluoromethyl- 17-(3-pyridyl)androsta- 16-en-3β-ol
and their acid addition salts and 3-esters.

Insofar as certain compounds within formula (1) are known per se and these are compounds which are less easy to prepare than many of the others, a preferred class of compounds of formula (1) is those which do not have a 3β-alkoxy group, a 14, 15-double bond or a 15-ester group.

The compounds of formula (1) can be prepared by a method which is in itself novel and inventive. Starting from a 17-oxo compound of general formula (4):

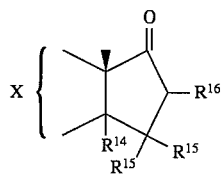
(4)

wherein X, $R^{14}$, $R^{15}$ and $R^{16}$ are as defined above and any other oxo groups and hydroxy groups in the molecule are first appropriately protected, the method comprises replacing the 17-hydroxy group of compound (4) in its enol form by a leaving group (L) which is capable of being replaced by a 3-pyridyl group in a palladium complex-catalysed cross-coupling reaction with a pyridyl ring-substituted boron compound of formula (5):

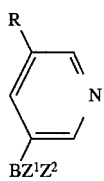
(5)

wherein $Z^1$ and $Z^2$ independently represent hydroxy or alkoxy or alkyl of 1–4 carbon atoms each, preferably 1–3 carbon atoms, most preferably ethyl or methoxy, or $Z^1$ and $Z^2$ together represent an alkylenedioxy group of 2 or 3 carbon atoms and R is as defined above and carrying out said cross-coupling reaction.

The palladium complex-catalysed cross-coupling reaction of the 17-substituted steroid with the boron compound is believed to involve the steps indicated in the following illustrative reaction scheme 1 (Py=3-pyridyl). The pyridyl anionic species is provided by the boron compound.

Scheme 1

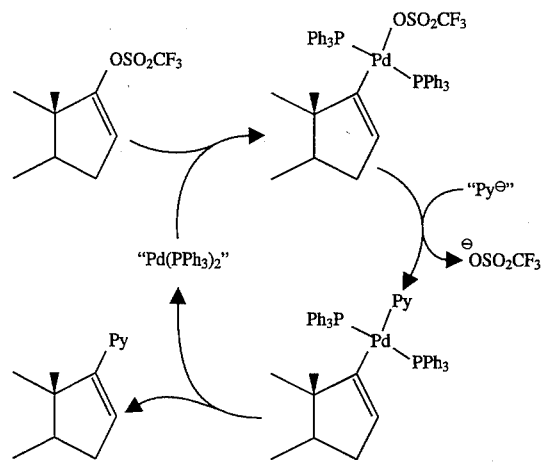

The replacement of the 17-enol group can be, for example, to form a 16,17-ene trifluoromethanesulphonate ("triflate") of formula (6):

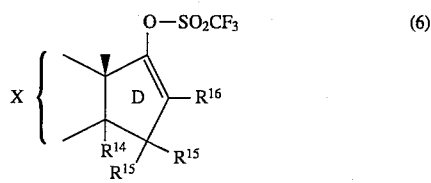
(6)

or a 17-iodo or bromo-16,[17]-ene (a "vinyl halide") of formula (7):

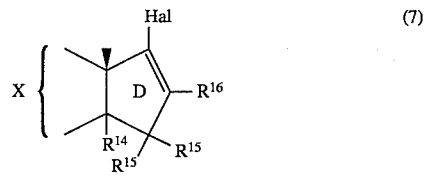
(7)

(Hal = I or Br)

Compounds of formula (6) can be prepared by reacting the 17-oxo compound of formula (4) with an enol ester-forming trifluoromethanesulphonic acid derivative such as the anhydride, see S. Cacchi, E. Morera and G. Omar, Tetrahedron Letters, 25, 4821 (1984). The 17-oxo compound can be considered notionally to exist in the enol form, the reaction being one of esterification of the enol.

For the preparation of the 17-position derivatives of formula (6) or (7) any necessary protection of other groups in the molecule may be first carried out. For example in the triflate route hydroxyl groups are conveniently protected as their acetates, whilst in the vinyl halide route the 3-oxo group of steroids can be selectively protected as their perfluorotolyl enol ethers, see M. Jannan and R. McCague, J. Chem. Soc. Perkin Trans. 1, 1129 (1987).

Compounds of formula (7) can be prepared by first hydrazinating the 17-oxo compounds of formula (4) by a standard method to form the 17-hydrozone, which is then reacted with bromine or iodine in the presence of an amine or guanidine base, see D. Barton, G. Bashiardes and J. Fourrey, Tetrahedron Letters, 24, 1605 (1983).

The 17-position derivative (whether triflate or vinyl halide) is then reacted with the boron compound of formula (5) using as catalyst a palladium(O) phosphine complex, for example tetrakis(triphenylphosphine)palladium(0), or a palladium (II) phosphine complex which is reducible in situ to a palladium(O) phosphine species, especially bis(triphenylphosphine)palladium (II) chloride.

SUMMARY OF THE INVENTION

The vinyl halide route, via a compound of formula (7), is particularly well suited to the preparation of 3β-acyloxy-16,17-ene-17-(3-pyridyl) steroids, especially the preferred compound, 3β-acetoxy-17-(3-pyridyl)androsta-5,16-diene, of formula (8):

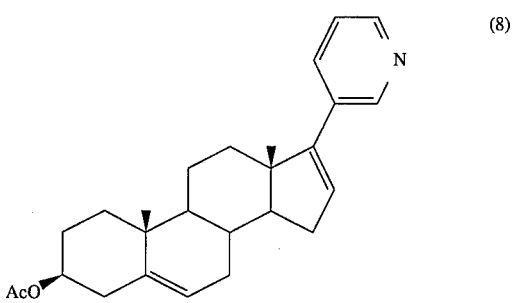

(8)

but using the unprotected 3β-hydroxy compound as starting material. By-products can be reduced either (a) by keeping the proportion of organoboron compound (borane) used in the cross-coupling reaction within the range 1.0 to 1.2 equivalents per equivalent of steroid or (b) by crystallising the reaction product of the cross-coupling reaction from a mixture of acetonitrile and methanol. This route via the vinyl iodide intermediate is therefore amenable to large scale synthesis, and is shown in Scheme 2 below.

steroid, wherein the 3β-(lower acyloxy) group of the steroid has from 2 to 4 carbon atoms, which comprises subjecting a 3β-hydroxy- 16,17-ene-17-iodo or -bromo steroid to a palladium complex-catalysed cross-coupling reaction with a (3-pyridyl)-substituted borane, in which the pyridine ting is substituted at the 5-position by an alkyl group of 1 to 4 carbon atoms or is unsubstituted thereat, especially with a said borane of formula (5), wherein R is a hydrogen atom or an alkyl group of 1–4 carbon atoms and $Z^1$ and $Z^2$ independently represent hydroxy or alkoxy or alkyl or 1–3 carbon atoms each or $Z^1$ and $Z^2$ together represent an alkylenedioxy group of 2 or 3 carbon atoms, in a proportion of at least 1.0 equivalent of boron compound per equivalent of steroid, in an organic liquid, which is a solvent for the 3β-hydroxy steroidal reaction product, and optionally esterifying the 3β-hydroxy reaction product to the 3 13-acyloxy ester, which method comprises feature (a) or (b) above.

Preferably the vinyl iodide or bromide is unsubstituted in the 14, 15 and 16-positions, in which case it can be prepared from dehydroepiandrosterone (DHEA). In the hydrazination it is preferable to use hydrazine hydrate together with a catalytic amount of a proton provider which is most preferably hydrazine sulfate.

The hydrazone is preferably iodinated with iodine or brominated with bromine in the presence of a strong base such as a tetraalkylguanidine, especially tetramethylguanidine which is cheaply and readily available.

In the cross-coupling reaction, the boron compound is preferably a diethylborane or a dimethoxyborane ($Z^1=Z^2$=Et or OMe). Other boranes include those in which the boron atom is part of a cyclic ether ring e.g. as in $Z^1$, $Z^2$=1,2-ethylenedioxy or 1,3-propylenedioxy. In embodiment (a) of

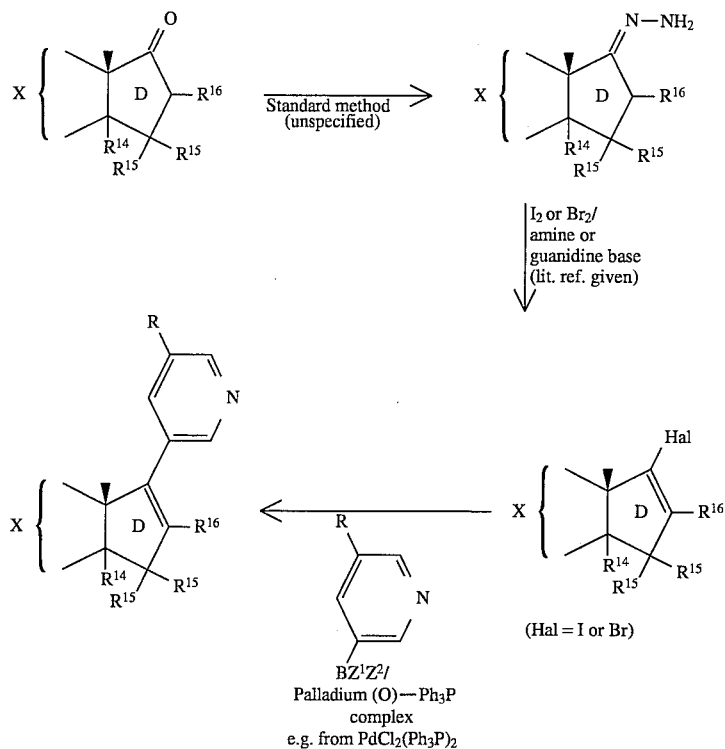

Scheme 2

The principle of this aspect of the invention may be expressed as a method of preparing a 3β-hydroxy- or 3β-(lower acyloxy)-16,17-ene-17-(3-pyridyl)-substituted this aspect of the invention the proportion of borane added is at least 1.0, but no more than 1.2 equivalents of boron per equivalent of steroid, preferably about 1.1, but in the embodiment (b) a higher proportion is preferred, e.g. from 1.2:1 to 1.5:1 equivalents of boron compound to steroid. The higher proportion will give the better yield of product but also more of the contaminating boron, phosphine and/or palladium compounds. According to embodiment Co), however, these are removed with the acetonitrile solvent. In either embodiment, the palladium compound is a palladium (0) phosphine complex such as tetrakis(triphenylphosphine) palladium (0) or a compound reducible to a palladium (0) phosphine species, especially bis(triphenylphosphine) palladium (II) chloride. The reaction vessel is preferably purged with an inert gas, especially argon or nitrogen, to minimize the possibility of oxidation with a corresponding redox reduction of palladium to the metallic state.

The cross-coupling reaction is preferably carried out in two phases, one aqueous, one organic. The organic phase comprises an organic solvent for the 3β-hydroxy steroidal reaction product, especially tetrahydrofuran (THF). Other cyclic ethers such as dioxane could be used in place of THF. Preferably, a nucleophilic activator, such as sodium carbonate, is used, in which case it is normally present in the aqueous phase. After the reaction, inorganic salts can be removed by first adding another organic solvent, preferably diethyl ether, which is a solvent for the organoboron contaminants produced in the reaction product, and miscible with the first-mentioned organic solvent (e.g. THF), but immiscible with water, whereafter the organic, e.g. THF-diethyl ether, phase and water (aqueous phase) can be separated. After this separation, various work-up procedures are operable. In one procedure, particularly suited to embodiment (a), the THF and diethyl ether are removed, e.g. evaporated as a mixture, and the remaining reaction product is washed with a third organic solvent, which can be diethyl ether, preferably cooled to below room temperature, most especially to 10° C. or lower. The third organic solvent is one in which the 3β-hydroxy steroid reaction product has a low solubility and which, importantly, removes the organoboron compounds (and also the contaminating phosphine and palladium compounds). Diethyl ether is preferred.

A different work-up procedure, used in embodiment (b), comprises crystallisation from acetonitrile/methanol. Acetonitrile is a preferred crystallisation solvent to keep boron compound as well as palladium compound in solution and is therefore used in an excess over methanol e.g. an excess of at least 5:1 and preferably about 8:1 by volume.

To prepare the 3β-acyloxy (alkylcarbonyloxy) compounds, of which the acetoxy compound is preferred, standard acylating (acyl-esterification) agents such as acetyl, propionyl or butyryl chloride or anhydride can be used. The final esterification product may be crystallised direct from hexane, rather than from ethanol/water followed by hexane. Preferably, the work-up procedure comprises reverse phase chromatography, i.e. using a relatively lipophilic solid phase. In this procedure, the chief by-product, a bis-steroidal compound, is preferentially retained on the solid phase and can be eluted with a good separation from the desired product.

Further compounds of the invention can be prepared by standard steroid to steroid inter-conversion chemistry, so long as the D-ring chemical structure is not affected thereby. If the D-ring structure is likely to be affected, it would usually be necessary to prepare the desired compound de novo, i.e. by choosing the appropriate starting compound of formula (4), protected if necessary, and carrying out the reactions of 17-substitution of the eno 1 and cross-coupling with the boron compound as described above.

By way of example, the 3-esters of asteroid 3-ol with an alkanoic acid of 1 to 6 carbon atoms, or a cycloalkanoic acid or aralkanoic acid such as phenylacetic or phenylpropionic acid, an aroic acid such as benzoic acid, or other simple organic acid such as methanesulphonic acid, can be converted into the 3-ol or the 3-ol to the 3-ester. Other examples of simple conversions which would not affect the D-ring structure are i) Oppenauer oxidation using cyclohexanone and aluminium isopropoxide to convert 3-hydroxy to 3-oxo steroids and notably $\Delta^{5,6}$-hydroxy to $\Delta^{4,5}$-3-oxo steroids;

ii) Wittig olefination to convert oxo groups to methylene groups [D. D. Evans et at., J. Chem. Soc., 4312–4317, (1963)];

iii) Oxidation of $\Delta^5$-3β-hydroxy to $\Delta^4$-3,6-dione steroids using N-methylmorpholine N-oxide and tetra-n-propylammonium perruthenate catalyst [M. Moreno et al., Tetrahedron Letters, 39.2, 3201–3204, (1991)];

iv) 6-Methylenation of 2-3-oxo steroids using formaldehyde dimethylacetal [K. Annen et al., Synthesis, 34–40 (1982)];

v) Conversion of $\Delta^4$-3-oxo to 4,4-dimethyl-$\Delta^5$-3-oxo, $^{1,4}$-3-oxo, $\Delta 1,4,6$-3-oxo 7α-methyl-$\Delta^4$-3-oxo, 4,6-3 -oxo, 6-chloro-$\Delta$-4,6-3-oxo, $\Delta^{2,4}$-2,3-isoxazole, 6α-methyl-$\Delta^4$-3-oxo and $\Delta^4$-3-desoxy; $\Delta^5$-3$\Delta$-ol to 5α-fluoro-6-oxo, 5α,6,6-trifluoro, 6,6-difluoro and 6α-fluoro-$\Delta^4$-3-oxo; and 11-oxo to 11-hydroxy and $\Delta^{9,11}$ steroids [D. Lednicer and L. A. Mitscher, The Organic Chemistry of Drug Synthesis, Is. 2 and 3, Wiley (1980 and 1984)] or vi) Electrophilic fluorination of steroids using N-fluoropyridinium reagents [T. Umenoto et al., Organic Synthesis 69, 129–143 (1990)].

The compounds of formula (1) may be prepared as salts, e.g. the hydrochloride and converted to the free base form and thereafter to such other conventional pharmaceutically acceptable salts as acetates, citrates and lactates, as may seem appropriate.

The present invention also provides a pharmaceutical composition which comprises a therapeutically effective amount of a compound of the invention, in association with a therapeutically acceptable carrier or diluent. The composition of the invention can, for example, be in a form suitable for parenteral (e.g. intravenous, intramuscular or intracavital), oral, topical or rectal administration. Particular forms of the composition may be, for example, solutions, suspensions, emulsions, creams, tablets, capsules, lipsomes or micro-reservoirs, especially compositions in orally ingestible or sterile injectable form. The preferred form of composition contemplated is the dry solid form, which includes capsules, granules, tablets, pills, boluses and powders. The solid carrier may comprise one or more excipients, e.g. lactose, tillers, disintegrating agents, binders, e.g. cellulose, carboxymethylcellulose or starch or anti-stick agents, e.g. magnesium stearate, to prevent tablets from adhering to tabletting equipment. Tablets, pills and boluses may be formed so as to disintegrate rapidly or to provide slow release of the active ingredient.

The present invention also includes a method of treating androgen- and oestrogen-dependent disorders, especially tumours, and most especially prostatic tumours, in the mammalian body, which comprises administering a compound of the invention to a mammalian patient in a therapeutically elective dose, e.g. in the range 0.001–0.04 mmole/kg body weight, preferably 0.001–0.01 mmole/kg, administered daily or twice daily during the course of treatment. This works out (for humans) at 20–800 mg/patient per day. The preferred use is in treating prostatic cancer. Another use is in treating breast cancer.

The following Examples illustrate the invention.

EXAMPLE 1

(a) 3β-Acetoxyldrosta-5,16-dien-17-yl trifluoromethanesulphonate

To a stirred solution of dehydroepiandrosterone-3-acetate (24.8g, 75 mmol) in dry dichloromethane (500 ml) containing 2,6-di-1-butyl-4-methylpyridine ( 18.5g, 90 mmol) was added trifluoromethanesulphonic anhydride (12.6 ml, 75 mmol). After 12 h the mixture was filtered and washed with water (50 ml), dried ($MgSO_4$), and the solvent evaporated. Chromatography, on elution with light petroleum-dichloromethane (6:1), gave firstly androsta-3,5,16-trien-17-yl trifluoromethanesulphonate (3.02g, 10%) as an oil. $^1$H-NMR($CDCl_3$) inter alia δ 0.99 (3H,s, 18-$CB_3$), 1.02(3H,s, 19-$CH_3$), 5.39(1H,m,6-H), 5.59(1H,m, 16-H), 5.62(1H,m,3-H), 5.93(1H,dm,J 9.4Hz,4-H); MS m/z 402M$^-$). Further elution with light petroleum-dichloromethane (3:1) afforded the title compound (20.1 g, 58%) which crystallised from hexane, m.p. 75°–76° C. $^1$H-NMR($CDCl_3$) inter alia δ 1.00(3H,s,18-$CH_3$), 1.06(3H, s,19-$CH_3$), 2.04(3H,s, $CH_3CO_2$), 4.59(1H,m,3α-H), 5.39(1H,dm,J 4.9 Hz,6-H), 5.58(1H,m, 16-H). Anal. Calcd: C,57.13; H,6.32; S,6.93. Found: C,57.29; H,6.31; S,6.96%.

(b) 3β-Acetoxy-12-(3-pyridyl)androsta-5,16-diene

Diethyl(3-pyridyl)borane (3.38g, 23 mmol) from Aldrich Chemical Co. Ltd. was added to a stirred solution of 3 β-acetoxyandrosta-5,16-dien- 17-yl trifluoromethanesulphonate (6.94 g, 15 mmol) in THF (75 ml) containing bis(triphenylphosphine)palladium(II)chloride (0.105 g, 0.15 mmol). An aqueous solution of sodium carbonate (2M, 30 ml) was then added and the mixture heated, with stirring, by an oil bath at 80° C. for 1 h, and allowed to cool. The mixture was partitioned between diethyl ether and water, the ether phase was dried ($Na_2CO_3$), filtered through a short plug of silica, and concentrated. Chromatography, on elution with light petroleum- diethyl ether (2:1), afforded the title compound (4.95 g, 84%) which crystallised from hexane, m.p. 144°–145° C., $^1$H-NMR($CDCl_3$) inter alia δ 1.05(3H,s, 19-$CH_3$), 1.08(3H,s, 18-$CH_3$), 2.04(3H,s,$CH_3CO_2$), 4.60(1H,m,3α-H), 5.42(1H,dm, J 4.7Hz,6-H), 5.99(1H,m, 16-H), 7.23(1H,m,Py 5-H) 7.65(1H,m,Py 4-H), 8.46(1H,m, Py 6-H), 8.62(1H,m,Py 2-H). Anal. Calcd: C, 79.75; H, 8.50; N, 3.58. Found: C, 79.78; H, 8.52; N, 3.54%.

EXAMPLE 2

17-(3-Pyridyl)androsta-5.16-dien-3β-ol

To a solution of 3β-acetoxy-17-(3-pyridyl)androsta-5,16-diene (4.90g, 12.5 mmol) in methanol (50 ml) was added an aqueous solution of sodium hydroxide ( 10% w/v, 10 ml) and the mixture heated, with stirring, on an oil bath at 80° C. for 5 min., then allowed to cool. The mixture was poured into water, neutralised with hydrochloric acid (1M), rebasified with sainted sodium bicarbonate solution, and extracted with hot toluene (3×100 ml). The toluene extracts were combined, dried ($Na_2CO_3$), and concentrated. Chromatography, on elution with toluene-diethyl ether (2:1 ) afforded the title compound (3.45 g, 79%) which crystallised from toluene, mp 228°–229° C.; $^1$H-NMR ($CDCl_3$ inter alia δ1.05(3H,s, 19-$CH_3$), 1.07(3H,s,18-$CH_3$), 3.54(1H,m,3α-H), 5.40(1H,dm,J 5.0 Hz, 6-H), 5.99(1H,m, 16-H), 7.22(1H, m,Py5-H), 7.65(1H,m,Py 4-H), 8.46(1H,m,Py 6H), 8.62(1H, m,Py 2-H), Anal. Calcd: C, 82.47; H, 8.94; N, 4.01. Found: C, 82.40; H, 8.91; N. 3.97%.

EXAMPLE 3

17-(3-Pyridyl)androsta-3,5,16-triene

The method followed that described in Example 1, using in step (b) diethyl(3-pyridyl)borane (0.88g, 6.0 mmol), androsta-3,5,16-trien-17-yl trifluoromethanesulphonate (2.01g, 5.0 mmol), prepared in step (a), THF (25 ml), bis(triphenylphosphine)palladium(II) chloride (35 mg, 0.05 mmol), and aqueous sodium carbonate (2M, 10 ml). Chromatography, on elution with dichloromethane, afforded the title compound (1.39 g, 84%) which crystallised from hexane, m.p. 110°–112° C. $^1$H-NMR ($CDCl_3$) inter alia δ 1.02(3H,s,19-$CH_3$), 1.07(3H,s,18-$CH_3$), 5.44(1H,m,6-H), 5.61(1H,m,3-H), 5.95(1H,dm, J 9.8 Hz, 4-H), 6.01(1H,m, 16-H), 7.23(1H,m,Py 5-H), 7.66(1H,m,Py 4-H), 8.46(1H,m, Py 6-hr), 8.63(1H,m,Py 2-H); MS m/z 331 (M$^+$).

EXAMPLE 4

(a) 3-[2,3,5,6-tetrafluoro-4-(trifluoromethyl)phenoxy]androsta-3,5,16-trien- 17-yl trifluoromethanesulphonate The method followed that described in Example 1 (a) but using 3-[2,3,5,6-tetrafluoro-4-(trifluoromethyl)phenoxy]androsta-3,5-dien-17-one (5.03 g, 10 mmol), prepared as described in M. Jannan and R. McCague, J. Chem. Soc., Perkin Trans. 1, 1129 (1987), dichloromethane (80 ml), 2,6-di+butyl-4-methylpyridine (2.87g, 14 mmol), and trifluoromethanesulphonic anhydride (1.85 ml, 11 mmol). Chromatography, on elution with light petroleum- dichloromethane (10:1), afforded the title compound (1.93 g, 30%) which crystallised from ethanol, m.p. 106°–107° C. $^1$H-NMR ($CDCl_3$) inter alia δ 1.02(6H,s,18 and 19-$CH_3$), 5.16(1H,s,4-H, 5.28(1H,m,6-H), 5.59-(1H,m,16-H); MS m/z 634(M$^+$).

(b) 3-[2,3,5,6-tetrafluoro-4-(trifluoromethyl)phenoxy]-17-(3-pyridyl)androsta-3,5,16-triene The method essentially followed that of Example 1(b) but using diethyl(3-pyridyl)borane (0.44 g, 3.0 mmol), 3-[2,3, 5,6-tetrafluoro-4-(trifluoromethyl)phenoxy]androsta-3,5, 16-trien-17-yl trifluoromethanesulphonate (1.27 g, 2.0 mmol), THF (10 ml), bis(triphenylphosphine)palladium(II) chloride (70 mg, 0.1 mmol), and aqueous sodium carbonate (2M, 5 ml). Chromatography, on elution with light petroleum-diethylether (3:1), afforded the title compound (0.82g, 73%) which crystallised from hexane, m.p. 166.0°–166.5° C. $^1$H-NMR ($CDCl_3$) inter alia δ 1.05(3H,s,19-$CH_3$), 1.07(3H,s,18-$CH_3$), 5.18(1H,s,4-H), 5.32(1H,m,6-H), 6.01(1H,m, 16-H), 7.23(1H,m,Py 5-H), 7.66(1H,m,Py 4-H, 8.47(1H,m,Py 6-H), 8.63(1H,m,Py 2-H). Anal. Calcd: C, 66.07; H, 5.01; N, 2.49; F, 23.60. Found: C, 65.97; H, 5.02; N, 2.47; F, 23.41%.

(c) 17-(3-Pyridyl)androsta-4,16-dien-3-one

To a solution of 3-[2,3,5,6-tetrafluoro-4-(trifluoromethyl)phenoxy]-17-(3-pyridyl)androsta-3,5,16-triene (0.423 g, 0.75 mmol) in THF (5 ml) was added ethanol (5 ml) followed by aqueous hydrochloric acid (1M, 5 ml) and the mixture heated, with stirring, by an oil bath at 65° C. for 48 h and allowed to cool. The mixture was poured into water (20 ml), neutralised with aqueous sodium hydroxide (1M), and extracted with diethyl ether (3×30 ml). The ether extracts were combined, dried ($Na_2CO_3$), and concentrated. Chromatography, on elution with diethyl ether, afforded the title compound (185 mg, 71%) which crystallised from diethyl ether, m.p. 148°–150° C. IR vmax 1674 cm$^{-1}$; $^1$H-NMR($CDCl_3$) inter alia δ 1.07(3H,s,18-$CH_3$), 1.24(3H, s,19-CB₃), 5.76(1H,m,Py 6-H), 5.99(1H,m,16-H), 7.23(1H, m,Py 5-H), 7.64(1H,m,Py 4-H), 8.47(1H,m,Py 6-H), 8.62(1H,m,Py 2-H); MS m/z, 347 (M⁺).

EXAMPLE 5

(a) 3-Acetoxyestra-1,3,5[10],16-tetraen-17-yl trifluoromethanesulphonate

The method followed that described in Example 1(a), but using oestrone-3-acetate (4.69 g, 15 mmol), dichloromethane (120 ml), 2,6-di-t-butyl4-methylpyridine (4.00 g, 19.5 mmol), and trifluoromethanesulphonic anhydride (2.8 ml, 16.5 mmol). Chromatography, on elution with light petroleum4-chloromethane (3:1 ), afforded the title compound (5.21 g, 78%). $^1$H-NMR(CDCl$_3$) inter alia δ 1.00(3H, s,18-CH$_3$), 2.29(3H,s,CH$_3$-CO$_2$), 5.62(1H,m, 16-H), 6.81($^1$H,m,ArH), 6.85(1H,m,ArH), 7.26(1H,m,ArH). Anal. Calcd. for C$_{21}$H$_{23}$O$_5$F$_3$S$_1$·½ H$_2$O: C, 55.62; H, 5.34. Found: C, 55.58: H, 5.14%.

(b) 3-Acetoxy-17-(3-pyridyl)estra-1,3,5[10],16-tetraene

The method followed that described in Example 1 (b), but using diethyl(3-pyridyl)borane (1.65 g, 11.2 mmol), 3-acetoxyestra- 1,3,5[10], 16-tetmen-17-yl trifluoromethanesulphonate (3.56 g, 8.0 mmol), THF (40 ml), bis(triphenylphosphine)palladium(II) chloride (56mg, 0.08 mmol), and aqueous sodium carbonate (2M, 15 ml).

Chromatography, on elution with light petroleum-diethyl-ether (2:1) afforded the title Compound (2.40 g, 80%). $^1$H-NMR(CDCl$_3$) inter alia δ 1.04(3H, s,18-CH), 2.29(3H, s, CH$_3$CO$_2$), 6.03(1H,m, 16-H), 6.82(1H,m,ArH), 6.85(1H,m, ArH), 7.24(1H,m,Py 5-H), 7.29(1H,m,ArH), 7.69(1H,m,Py 4-H), 8.48(1H,m,Py 6-H), 8.65(1H,m,Py 2-H); MS m/z 373. (M⁺).

EXAMPLE 6

17-(3-Pyridyl)estra-1,3,5[10],16-tetraen-3-ol

The method followed that described in Example 2, but using 3-acetoxy-17-(3-pyridyl)estra-1,3,5[10],16-tetraene (2.368, 6.3 mmol), methanol (40 ml), aqueous sodium hydroxide (10% w/v, 5 ml), and the mixture was heated at 80° C. for 10 min. Chromatography, on elution with toluene-methanol (8:1), afforded the title compound (1.40 g, 67%) which crystallised from toluene, m.p. 256°–258° C.: $^1$H-NMR(DMSO) inter alia δ 1.01(3H,s, 18-CH$_3$), 6.15(1H,m, 16-H), 6.47(1 H,m,ArH), 6.52(1 H,m,ArH), 7.04($^1$H,m,ArH), 7.35(1H,m, Py 5-H), 7.79(1H,m,Py 4-H), 8.45(1H,m,Py 6-H), 8.62(1H,m,Py 2-H). Anal. Calcd: C, 83.34; H, 7.60; N, 4.23. Found: C, 83.39; H, 7.78; N, 4.06%.

EXAMPLE 7

3α-Acetoxy-17-(3-pyridyl)-5α-androst-16-ene

The method followed that described in Example 1, using in step (b) diethyl(3-pyridyl)borane (1.41 g, 9.6 mmol), 3,,-acetoxy- 5,,-androst-16-en-17-yl trifluoromethanesulphonate (3.44 g, 7.4 mmol), prepared from the 3α-acetoxy-5α-androstan-17-one by the method of step (a), THF (40 ml), bis(triphenylphosphine)palladium(II) chloride (52 mg, 0.07 mmol), and aqueous sodium carbonate (2M, 15 mmol). Chromatography, on elution with light petroleum-diethyl ether (2:1), afforded the title compound (2.39 g, 82%), $^1$H-NMR (CDCl$_3$) inter alia δ 0.85(3H,s,19-CH$_3$), 1.01(3H,s, 18-CH$_3$), 2.06(3H,s,CH$_3$CO$_2$), 5.02(1H,m,3β-H), 6.00(1H,m, 16-H), 7.24(1H,m,Py 5-H), 7.68(1H,m,Py 4-H), 8.47(1H,m,Py 6-H), 8.63(1H,m,Py 2-H); MS m/z 393 (M$_+$).

EXAMPLE 8

17-(3-pyridyl)-5α-androst-16-en-3α-ol

The method followed that described in Example 2, but using 3α-acetoxy-17-(3-pyridyl)-5α-androst-1,6-ene (2.33 g, 5.9 mmol), methanol (40 ml), aqueous sodium hydroxide (10% w/v, 8 ml), and the mixture was heated at 80° C. for 20 min. Chromatography, on elution with toluene-methanol (40:1), afforded the title compound (1.62 g, 78%) which crystallised from toluene, m.p. 198°–199° C.; $^1$H-NMR(CDCl$_3$) inter alia. δ 0.84(3H,s, 19-CH$_3$), 1.00(3H,s,18-CH$_3$), 4.06(1H,m,3β-H), 5.97(1H,m,16-H), 7.21(1H,m,Py 5-H), 7.64(1H,m,Py 4-H), 8.45(1H,m,Py 6-H), 8.61(1H,m, Py 2-H). Anal Calcd: C, 82.00; H,9.46; N,3.99. Found: C,81.78; H,9.47; N.3.96%.

EXAMPLE 9

17-(3-Pyridyl)-5α-androst-16-en-3-one

From a solution of 17-(3-Pyridyl)-5α-androst-16-en-3α-ol (1.05g, 3.0 mmol) in dry toluene (60 ml) and cyclohexanone (10 ml) was distilled off part of the solvent (20 ml) to eliminate moisture. After allowing to cool to 90° C., aluminium isopropoxide (1.02 g, 5.0 mmol) was added and the mixture heated under reflux for 90 min. then allowed to cool. The mixture was diluted with diethyl ether (250 ml), washed with aqueous trisodium citrate ( 15% w/v; 2×30 ml), dried (Na$_2$CO$_3$), and concentrated. Chromatography, on elution with toluene-methanol (40:1), afforded the title compound (0.90 g, 86%) which crystallised from toluene, m.p. 190°–192° C. IR vmax 1713 cm⁻; $^1$H-NMR (CDCl$_3$) inter alia δ 1.04 (3H,s,19-CH$_3$), 1.07 (3H,s, 18-CH$_3$), 5.98 (1M, 16-H), 7.22 (1H,m,Py 5-H), 7.64 (1H,m,Py 4-H), 8.46 (1 H,m,Py 6-H), 8.61 (1H,m,Py 2-H); MS m/z 349 (M+). Anal. Calcd: C,82.47; H,8.94; N,4.01. Found: C.82.00; H,8.94; N,3.84%

EXAMPLE 10 a) 3-(tert-Butyldimethylsiloxy)androsta-3,5-diene-11,17-dione

To a solution of adrenosterone (6.0 g, 20 mmol) in dry, dichloromethane (120 ml) was added triethylamine (8.4 ml, 60 mmol) followed by tert-butyldimethylsilyl trifluoromethanesulfonate (5.0 ml, 22 mmol) and the mixture stirred at room temperature for 3 h. The dichloromethane was evaporated and the residue redissolved in diethyl ether (100 ml), then allowed to stand for 30 min, after which time an oil separated. The ether phase was decanted off the oil and the solvent evaporated to give the title compound which was used directly in step (b). IR vmax 1705, 1747 cm⁻¹; $^1$H-NMR(CDCl$_3$) inter alia δ0.12 (6H,s,Me$_2$Si), 0.85 (3H,s,18-CH$_3$), 0.92 (9H,s,$^t$BuSi) 1.17(3H,s, 19-CH$_3$), 4.73 (1H,dm, J 6.9Hz, 6-H), 5.36 (1H,m,4-H).

b) 13-(tert-Butyldimethylsiloxy)-11-oxo-androsta-3,5,16-trien-17-yl trifluoromethanesulfonate To a solution of the product from step (a) in dry THF (100 ml), cooled to −78° C., was added a freshly prepared solution of lithium diisopropylamide [prepared by adding n-butyllithium (1.6M; 13.8 ml, 22 mmol) in hexane to a solution of diisopropylamine (3.1 ml, 22 mmol) in dry THF (25 ml) at −18° C.] and the resultant yellow solution stirred at −78° C. for 30 min. A solution of N-phenyltrifluoromethanesulfonimide (7.15 g, 20 mmol) in dry THF (20ml) was then added and after an additional 1 h. at −78° C. was allowed to reach ambient temperature. The reaction mixture was poured into water (200 ml) and extracted with diethyl ether (2×200 ml), the combined ether extracts were washed with water (20 ml), dried $Na_2CO_3$), and concentrated to give the title compound which was used directly in step (c). IR $\nu$max 1710 cm$^4$, $^1$H-NMR (CDCl$_3$) inter alia $\delta$0.13 (6H,S, Me$_2$Si), 0.92 (9H,s,$^t$BU Si), 1.35 (6H,2s, 18-CH$_3$ and 19-C.H$_3$), 4.75 (1 H,m,6-H) 5.38 (1H,s,4-H), 5.68 (1H,m, 16-H).

c) 3-(tert-Butyldimethylsiloxy)-17-(3-pyridyl)androsta-3,5,16-trien- 11-one

The method essentially followed that described in Example 1 (b), but using the 13-(tert-butyldimethylsiloxy)-11-oxo-androsta-3,5,16-trien-     17-yltrifluoromethanesulfonate from step (b), diethyl (3-pyridyl)borane (3.53 g, 24 mmol), THF (100 ml), bis(triphenylphosphine)palladium (II) chloride (280 mg, 0.4 mmol), and aqueous sodium carbonate (2M;50 ml). Following work-up as described in Example 1 (b) the title compound was obtained, which was used directly in step (d). IR $\nu$max 1705 cm$^1$, $^1$H-NMR (CDCl$_3$) inter alia $\delta$0.13 (3H,s,Me$_2$Si), 0.93 (9H,s,$^t$BuSi), 0.99 (3H,s,18-CH$_3$), 1.18 (3H,s,19-CH$_3$), 4.75 (1H,m,6-H) 5.37 (1H,m,4-H), 6.09 (1H,m, 16-hr), 7.26 (1H,m,Py 5-H), 7.62 (1H,m,Py 4-H), 8.50 (1H,m,Py 6-hr), 8.60 (1H,m,Py 2-H). MS m/z, 475 (M+).

d) 17-(3-Pyridyl)androsta-4,16-diene-3,11-dione

To a solution of the product from step (c) in wet THF (60 ml) was added a solution of tetrabutylammonium fluoride (1.0M; 10 ml, 10 mmol) in THF, and the mixture stirred at room temperature for 12 h. The mixture was partitioned between diethyl ether and water basified with saturated aqueuous sodium bicarbonate, the ether phase isolated, dried (Na$_2$CO$_3$), and concentrated. Chromatography, on elution with diethyl ether, afforded the title compound (4.30 g, 60% overall yield from adrenosterone) which crystallised from diethyl ether, m.p. 181°–183° C.

IR $\nu$max 1669, 1703 cm$^{-1}$ $^1$H-NMR(CDCl$_3$) inter alia $\delta$1.02 (3H,s, 18-CH$_3$), 1.45 (3H,s,19-CHD, 5.76 (1H,s,Py 4-H), 6.08 (1H,m, 16-H) 7.24 (1H,m,Py 5-H), 7.59 (1H,m, Py 4-H),8.50 (1H,m,Py 6-H), 8.59 (1H,m,Py 2-H). MS m/z 361 (M+). Anal Calcd: C, 79.74; H,7.53: N,3.88. Found: C,79.58; H,7.57; N,3.89%.

EXAMPLE 11

3-Acetoxy-17-(3-pyridyl)androsta-3,5,16-triene 17-(3-pyridyl)androsta-4,16-dien-3-one (174 mg, 0.50 mmol) was dissolved in isopropenyl acetate (2 ml). p-Toluenesulfonic acid (130 mg, 0.68 mmol) was then added and the mixture heated at 80° C. for 12 h. After allowing to cool the mixture was poured into diethyl ether, washed with saturated aqueous sodium bicarbonate, dried (Na$_2$CO$_3$) and concentrated. Chromatography on elution with light petroleum—diethyl ether (1:1), afforded the title compound (86 mg, 44%), IR $\nu$max 1755 cm$^{-1}$, $^1$H-NMR (CDCl$_3$) inter alia $\delta$1.05 (6H,s,18-CH$_3$ and 19-CH$_3$), 2.15 (3H,s,COCH$_3$) 5.44 (1 H,m,6-H), 5.72(1H,m,4-H), 6.00 (1H,m,16-H), 7.25 (1H, m,Py 5-H), 7.66 (1H,m,Py 4-H), 8.47 (1H,M,Py 6H), 8.63 (1H,m,Py 2-H). MS m/z 389 (M+).

EXAMPLE 12

6α-Fluoro-17-(3-pyridyl)androsta-4,16-dien-3-one and

EXAMPLE 13

6α-Fluoro-17-(3-pyridyl)androsta-4,16-dien-3-one

To a solution of 3-acetoxy-17-(3-pyridyl)androsta-3,5,16-triene (80 mg, 0.21 mmol) in dry dichloromethane (2 ml) was added N-fluoropyridinium trifluoromethanesulfonate (180 mg, 0.73 mmol) and the mixture heated under reflux for 12 h. The mixture was diluted with diethyl ether (30 ml), washed with dilute aqueous sodium hydroxide (0.5M; 2×5 ml), dried Na$_2$CO$_3$), and concentrated. $^1$H and $^{19}$-NMR at this stage showed the 6-fluorinated products were formed as a 3:2 mixture of the β and α-epimers. Chromatography, on elution with light petroleum-diethyl ether (1:2), gave firstly:-i) the title 6β-epimer (13 mg), 17%) as white crystals, m.p. 167°–169° C. IR $\mu$max 1684 cm$^{-1}$; $^1$H-NMR (CDCl$_3$) inter alia $\delta$1.11 (3H,s,18-CH$_3$), 1.37 (3H,s, 19-CH$_3$), 5.06 (1H,dd, $J_{H-H}$2.4 Hz, $J_{H-F}$49Hz, 6β-H), 5.92 (1H,m,4-H), 6.01 (1H,m, 16-H), 7.24 (1H,m,Py 5-H), 7.65 (1H,m,Py 4-H), 8.48 (1H,m,Py 6-H), 8.63 (1H,m,Py 2-H). $^{19}$F-NMR $\delta$-165.9 (dt, $J_{h-F}$49 Hz, 6β-F). MS m/z 365 (M+).

Further elution afforded:

ii) The title 6α-epimer(8 mg, 11%) as white crystals, m.p. 167°–169° C., IR $\nu$max 1681 cm$^{-1}$; $^1$H-NMR (CDCl$_3$) inter alia $\delta$ 1.07 (3H,s, 18-CH$_3$), 1.24 (3H,s, 19-CH$_3$), 5.18 (1H,dm, $J_{H-F}$ 48 Hz, 6β-H), 5.98 (ZH,m,4-H and 16-H), 7.26 (1H,m,Py 5-H), 7.64 (1H,m, Py 4-H), 8.40 (1H,m,Py6-H), 8.63 (1H,m,Py 2-H). $^{19}$F-NMR (CDCl$_3$)$\delta$-183.9 (d, $J_{H-F}$ 48 HZ, 6α-F). MS m/z 365 (M+).

EXAMPLE 14

17-(3-pyridyl)androsta-4,16-dien-3-one (via Oppenauer Oxidation)

This Example illustrates a better method of preparing the compound already prepared in Example 4. The method followed that described in Example 9, but using 17-(3-pyridyl)androsta-5, 16-dien-3β-ol (1.05g, 3.0 mmol). Chromatography, on elution with toluene-methanol (20:1), afforded the title compound (0.85g, 82%), which crystallised from diethyl ether, m.p. 148°–150° C. Spectroscopic data was identical to that given in Example 4(c).

Anal. Calcd: C,82.95; H,8.41; N,4.03

Found: C,83.00; H,8.50; N,3.99%

EXAMPLE 15

17-(3-pyridyl)androsta-4,16-dien-3-one oxime

To a suspension of 17-(3-pyridyl)androsm-4,16-dien-3-one (125 mg, 0.36 mmol) in ethanol (2 ml) was added hydroxylamine hydrochloride (50 mg, 0.72 mmol), followed by pyridine (0.2 ml), and the mixture heated under reflux for 1 h. then allowed to cool.

The solvent was evaporated and the crystalline product triturated under water, collected on a sinter, washed with cold water, and dried in vacuo to give the title oxime as a 1:1 mixture of syn and anti geometric isomers. $^1$H-NMR$^{CDCl_3}$) inter alia δ 1.06 (3H,s, 18-CH$_3$, 1.13 (3H,s, 19-CH$_3$), 5.75 and 5.80 (1H,2 m, isomeric 4-H), 6.01 (1H,m, 16-H), 7.26 (1H,m,Py 5H), 7.68 and 7.88 (1H, 2 m, isomeric Py 4-H), 8.48 and 8.53 (1H, 2 m, isomeric Py 6-H), 8.63 (1H,m,Py 2-H). MS m/z 362 (M+).

EXAMPLE 16

17-(3-pyridyl)androsta-4,16-diene-3,6-dione

To a solution of 17-(3-pyridyl)androsta-5,16-dien-3β-ol (350 mg, 1.0 mmol) in dry dichloromethane (10 ml) was added N-methylmorphine N-oxide (351 mg, 3.0 mmol) followed by 400 mg of freshly dried and powdered 4 Å molecular sieves and the mixture stirred for 10 min. Tetrapropylammonium perruthenate catalyst (35 mg), 0.1 mmol) was then added, the reaction flask placed in an ultrasonic bath, and the mixture irradiated whilst maintaining the temperature between 20°–30° C. for 2 h. The mixture was then filtered, diluted with diethyl ether, washed with water, dried (Na$_2$CO$_3$), and concentrated. Chromatography, on elution with diethyl ether —ethyl acetate (5:1), afforded the title compound (26 mg, 7%) as white crystals m.p. 210°–212° C. IR vmax 1680 cm$^{-1}$; $^1$H-NMR (CDCl$_3$) inter alia 61.10 (3H,s,18-CH$_3$), 1.44 (3H,s, 19-CH$_3$), 4.42 (1H, m,enolic 2-H), 5.84 (1H,s,4-H), 6.01 (1H,m,16), 7.24 (1H, m,Py 5-H), 7.65 (1H,m, Py 4-H), 8.45 (1H,m,Py 4-H), 8.45 (1H,m,Py 2-H). FAB-MS MS m/z 362 (M+1).

EXAMPLE 17

3α-(Trifluoromethyl)-17-(3-pyridyl)androst-16-en-3β-ol

To a solution of 17-(3-pyridyl)androst-16-en-3-one (100 mg, 0.29 mmol) in THF (2 ml) cooled to 0° C. was added trifluommethyltrimethylsilane (200 μl, 1.3 mmol) followed by tetrabutylammonium fluoride trihydrate (10 mg, 0.03 mmol). After 30 min., dilute aqueous hydrochloric acid (1M; 1 ml) was added and the mixture stirred at room temperature for 12 h. The mixture was then basified with saturated aqueous sodium bicarbonate and extracted with diethyl ether. The three extracts were combined, dried (Na$_2$CO$_3$), and concentrated. Chromatography, on elution with light petroleum—diethyl ether (1:1), afforded the title compound (87 mg, 73%) which crystallised from toluene, m.p. 192°–193° C. $^1$H-NMR (CDCl$_3$ inter alia δ0.92 (3H,s,19-CH$_3$), 1.01 (3H,s,18-CH$_3$), 5.98 (1H,m,16-H), 7.22 (1H,m, Py 5-H), 7.64 (1H,m,Py 4-H),8.45 (1H,m,Py 6-H), 8.60 (1H,m,Py 2-H); $^{19}$F-NMR (CDCl$_3$) δ-79.1 (s,3α-CF$_3$). MS m/z 419 (M+).

Anal. Calcd: C,71.57; H,7.69; N,3.34; F,13.59

Found: C,71.67; H,7.71; N,3.25; F,13.30%

EXAMPLE 18

(a) Diethyl[3-(5-methylpyridyl)]borane

3-Bromo-5-methylpyridine, which can be prepared as described in the literature, e.g. L. van der Does and H. J. van Hertog, Rec. Trav. Chem. Pays Bas 84, 957–960 (1985) or R. A. Abramovitch and M. Saha, Can. J. Chem. 44, 1765–1771 (1966), is reacted with n-butyllithium, according to the method of M. Terashima et al., Chem. Pharm. Bull. 31, 4573–4577, (1983). The product is treated with triethylborane and then iodine.

(b) 17-[3-(5-Methylpyridyl)]androsta-5,16-dien-3β-ol

Diethyl [3-(5-methylpyridyl)]borane is reacted with 3β-acetoxyandrosta-5,16-dien-17-yl trifluoromethane sulphonate analogously to Example 1 (b) and the resulting 3β-acetate is hydrolysed with sodium hydroxide, analogously to Example 2, to yield the title compound.

The following Examples illustrate preparation of compounds of the invention by the vinyl halide route. In Example 19, the 3β-hydroxy product is produced without chromatography, by embodiment (a). In Example 20, the 3β-hydroxy product is not isolated, but in step (d) an impurity has been identified as a 16,17'-bis(steroidal) by-product. This can be removed by reverse phase chromatography, but now that the by-product has been identified, those skilled in the art will be able more easily to identify procedures which will remove it, without the need for chromatography. Further, it is believed that with the higher organoboron: steroid ratios suggested above, the side-reaction leading to this impurity will be reduced.

EXAMPLE 19

(a) Dehydroepiandrosterone-17-hydrazone

To a stirred solution of dehydroepiandrosterone (28.8 g, 0.1 mol) in ethanol (500 ml) was added hydrazine hydrate (19.5 ml, 0.4 mol), followed by a solution of hydrazine sulfate (65 mg, 0.5 mmol) in water (2 ml). After stirring for 3 days the mixture was poured into water (3 liters) to precipitate the product as a white crystalline solid. The product was collected by filtration on a sinter, washed with cold water (2×50 ml), then with Et$_2$O (50 ml). The product was then dried in vacuo, firstly over silica gel, and finally over P$_2$O$_5$, to give the title compound as a white crystalline solid (29.6 g, 98%).

Notes 1) The method of Schweder et al., p.202. compound No. 2 therein (using triethylamine) gave a very line crystalline product which was difficult to filter.

2) The method of Schweder et al. p. 203, compound No. 4 therein (using sodium acetate buffer) gave a slightly lower yield (96%) in trial experiments, whereas the modified procedure used above gave a product amenable for filtration, and in excellent yield (98%).

(b) 17-Iodo-androsta-5,16-dien-3β-ol

To a solution of iodine (53.3 g, 0.21 mol) in THF (2L), cooled by an ice/water bath to 0° C., was added 1,1,3,3-tetramethylguanidine (63 ml, 57.6 g, 0.50 mol).

A solution of dehydroepiandrosterone-17-hydrazone (30.25 g, 0.10 mol) in THF (750 ml) was then added slowly to the above iodine solution via a transfer needle over about 2 h, whilst maintaining the reaction temperature at 0° C.

After all the hydrazone solution was added, the mixture was filtered, and the filtrate concentrated. The remaining oil was then heated on an oil bath for 4 h, allowed to cool, and dissolved in $Et_2O$. The $Et_2O$ solution was washed with 1M HCl until the aqueous phase was acidic, washed with 0.5M NaOH, then 1M $Na_2SO_3$, and finally with water. The $Et_2O$ phase was separated, dried ($MgSO_4$), and concentrated to give the crude product. Recrystallisation from $Et_2O$/hexane (3:2) afforded the title compound as off-white crystals (35.8 g, 90%).

(c) 17-(3-Pyridyl)androsta-5,16-dien-3β-ol

Diethyl(3-pyridyl)borane (3.23 g, 22 mmol) from Aldrich Chemical Co. Ltd. was added to a stirred solution of 17-iodo-androsta-5,16-dien-3β-ol (7.96 g, 20 mmol) in THF (120 ml) containing bis(triphenylphosphine)palladium (II) chloride (140 mg, 0.2 mmol). An aqueous solution of sodium carbonate (2M, 50 ml) was then added and the mixture heated, with stirring, by an oil bath at 80° C. for 48 h, and allowed to cool.

The mixture was partitioned between $Et_2O$ and water the organic phase was separated, dried ($Na_2CO_3$) and twice concentrated from $EtO_2O$ by evaporation to remove THF (with $Et_2O$). The residual solid was then washed with $Et_2O$ (100 ml), the $Et_2O$ solution decanted off, and the remaining white solid recrystallised from toluene (3.94 g, 56%).

Notes 1) The time required for completion needs to be made longer than when using the vinyl triflate (48 h vs 1 h) since it has been found that the vinyl iodide reacts much more slowly.

2) It has been found that a smaller excess of borane than described in the earlier applications (for the vinyl triflate) aids in isolation of product.

3) The work-up procedure enables the product to be isolated without chromatography, thereby enabling scaling up.

(d) 3β-Acetoxy-17-(3-pyridyl)androsta-5,16-diene

To a stirred suspension of finely powdered 17-(3-pyridyl)androsta-5,16-dien-3β-ol (3.50 g, 10 mmol) in dry diethyl ether (150 ml) coning triethylamine (2,3 ml, 16 mmol) and dimethylaminopyridine (0.012 g, 0.1 mmol) was added acetyl chloride (1.0 ml, 14 mmol). The mixture was then stirred at ambient temperature for 12 h, over which time a thick whim precipitate of triethylammonium chloride had formed. The mixture was then filtered and the filtrate concentrated to afford the crude product which was recrystallised firstly from ethanol/water (1:1), then finally from hexane to afford the title compound (3.30 g, 84%).

EXAMPLE 20

(a) Dehydroepiandrosterone-17-hydrazone

Into a 10 L round-bottomed flask, fitted with a magnetic stirrer bar, was placed dehydroepiandrosterone (288 g, 1.0 mol) and ethanol (5.0 L). To the resultant stirred solution was added hydrazine hydrate (195 ml, 4.0 mmol), followed by a solution of hydrazine sulfate (0.65 g, 0.005 mmol) in water (20 ml) [note: the hydrazine sulfate dissolved in this volume of water at about 40° C.]. After stirring at room temperature for 5 days, water (4.5 L) was added, the mixture poured into water (10 L), and the white crystalline precipitate allowed to settle. The product was collected by filtration on a sinter, washed with cold water (2×500 ml), then with $Et_2O$ (2×500 ml). The product was then dried in vacuo, firstly over silica gel, and finally over $P_2O_5$, to give the title compound as a white crystalline solid, mp 204°–206° C. (284.8 g, 94%).

(b) 17-Iodo-androsta-5,16 dien-3β-ol

A 10 L round-bottomed flask, fitted with a magnetic stirrer bar, was charged with iodine (156.1 g, 0.615 mol), THF (4.0 L; GPR grade), and $Et_2O$ (2.0 L; BDH specially dried grade). The resultant stirred solution was cooled by an ice/water bath to 0° C. and 1,1,3,3-tetramethylguanidine (188 ml, 173 g, 1.50 mol) was added. A solution of dehydroepiandrosterone-17-hydrazone from step (a) (90.74 g, 0.30 mol) in THF (2.25 L) was then added slowly to the above iodine solution via a canula over about 2 h, whilst maintaining the reaction temperature at 0° C. [note: $N_2$ is evolved as the hydrazone is added to the iodine solution]. After all the hydrazone solution was added, the mixture was stirred for an additional hour and the precipitate allowed to settle [note: a precipitate of tetramethylguanidium iodide forms during the reaction]. The mixture was then filtered, and the filtrate concentrated to an oil on a rotary evaporator.

This reaction was carded out a total of three times, thus using in total 272.22 g (0.90 mol) of dehydroepiandrosterone-17-hydrazone from step (a). The concentrated residues from the three separate reactions were combined and heated on an oil bath for 4k, then allowed to cool [note: this converts any 17,17-diiodo by-product into the 17-vinyl iodide product]. This oil was then dissolved in $Et_2O$ (5 L), filtered, and further diluted with additional $Et_2O$ (4 L).

The $Et_2O$ solution was washed with aqueous HCl (1M; 3×500 ml)until the aqueous phase was acidic [note: the ether solution changes colour from brown to yellow when the aqueous phase remains acidified]then finally with water (500 ml). The $Et_2O$ phase was separated, dried ($MgSO_4$), and concentrated to a volume of 3 L, then left to allow the product to crystallise. The yellow crystals were collected by filtration on a sinter, washed with hexane (3×500ml) and dried under vacuum (335.4 g, 94%). Recrystallisation from ethanol-water (5:1) afforded the product as white crystals (297.3 g, 83%) mp 175°–176° C., lit. mp 173°–174° C.

(c) 17-(3-Pyridyl)androsta-5,16-dien-3β-ol

In a 2 L round-bottomed flask, fitted with a magnetic stirrer bar, was placed the steroidal 17-iodo product from step (b) (98.0 g, 0.246 mol) and this was dissolved in THF (1.1 L). The flask was paged with argon and bis(triphenylphosphine)palladium (II) chloride catalyst (1.73 g, 0.0025 mol) was added, followed by diethyl(3-pyridyl)borane (43.35 g, 0.295 mol). To the resultant orange THF solution was added an aqueous solution of sodium carbonate (2M; 500 ml). The flask was fitted with a reflux condenser, and the apparatus purged again with argon. The mixture was then heated under reflux (at about 80° C.) with stirring on a stirrer/heating mantle (Electrothermal MA) for 4 days [note: upon completion of the reaction the organic phase darkens in colour from orange to dark orange/brown], then allowed to cool. This reaction was carried out a total of three times, thus using a total of 294.0 g (0.74 mol) of the steroidal 17-iodo product from step (b). The reaction mixtures were combined and $Et_2O$ (5 L) added. The organic phase was separated, washed with water (2 L), and left to give a first crop of crystals which were collected by filtration on a sinter. The filtrate was concentrated and the residue redissolved in $Et_2O$ to afford a second crop of crystals. The aqueous phase and washings from the above work-up were extracted with hot toluene (2 L) on a steam bath and concentration of the toluene extracts afforded further product. The combined crude product from the above procedures was then dissolved in the minimum volume of hot methanol, filtered through a plug of "Celite" (Registered Trade Mark) and an equal volume of acetonitrile added to the methanol solution. The acetonitrile/methanol solution was then concentrated to half its original volume on a rotary evaporator and the solution left to crystallise. The resultant white crystals were collected by filtration on a sinter, washed with acetonitrile and dried in vacuo to constant weight (191.1 g, 74%), mp 202°–212° C. A second recrystallisation from toluene-methanol (50:1) afforded the product as white crystals (146.8 g, 57%) mp 214°–218° C., lit. mp 228°–229° C.

(d) 3β-Acetoxy-17-(3-pyridyl)androsta-5,16-diene

The following reaction was carded out in a 500 ml round-bottomed flask, fitted with a magnetic stirrer bar. To a suspension of the steroidal product from step (c) (26.5 g, 0.104 mmol) in dry pyridine (200 ml), was added acetic anhydride (75 ml) and the mixture stirred at room temperature for 24 h. The pyridine and excess acetic anhydride were removed on a rotary evaporator, initially with the water bath at 70° C., and finally at 80° C. for 30 min. The resulting oil was dissolved in $Et_2O$ (500 ml), washed with saturated aqueous $NaHCO_3$ (2×200 ml), dried ($Na_2CO_3$), and concentrated to an oil which crystallised on standing. $^1H$-NMR spectroscopy at this stage showed the product contained about 5% of a 16,17'-bi(steroidal) contaminant, 3β-acetoxy-16-(3'-11-acetoxyandrosta-5',16'-dien- 17'-yl)-17-(3-pyridyl)androsta-5,16-diene, which originated as a by-product from the coupling reaction of step (c).

The product was therefore further purified by preparative flash chromatography using a 9 cm diameter column, with silica stationary phase (Merck 15111), eluting with dicholoromethane. The by-product eluted first followed by the desired product, although the separation was incomplete. Fractions containing a significant amount of by-product were combined and subjected to further chromatographic purification.

The foregoing reaction and purification procedure was carried out a total of four times, thus using a total of 146 g (0.418 mol) of the steroidal product from step (c).

The product-containing dichloromethane fractions from the chromatographic purification were concentrated and recrystallised from hexane to afford white crystals which were dried in vacuo to constant weight. The total amount of product obtained was 136.0 g(83%).

The dichloromethane fractions containing the least by-product were combined, and following recrystallisation from hexane, afforded the title compound as white crystals with mp 142°–144° C. Analysis showed this material ("A") contained 6.8% w/w of the bis(steroidal) by-product.

A second crop of white crystals ("B") of the product, containing 21.8% w/w of bis(steroidal) by-product (25 g), was obtained.

The two products were purified using reverse phase chromatography. The column was packed with "LiChroprep" (Registered Trade Mark) RP-8 reverse-phase $C_8$ packing, Art. No. 9324, supplied by E. Merck, Darmstadt, Germany. The course of the chromatography was followed by UV detection at 253 nm, with purity checks by HPLC. Product "A" (10.17 g) was dissolved in 200 ml. hot acetonitrile and 40 ml. hot methanol, and, after being allowed to cool, the filtrate was applied to a 10 cm. diameter column containing about 500 g. of the packing. The eluant was 5% 0.05M aqueous ammonium acetate/95% v/v acetonitrile. 7.51 g. of product was recovered in fractions 4–10. Fractions (500 ml) 4–11 contained the product with some impurities, but not the bis-steroidal by-product. The eluant was changed to 2.5% acetic acid/95.5% v/v acetonitrile and then to 5% acetic acid/95% v/v acetonitrile. A pink colour seen in fractions 16 and 17 evidenced the bis-steroidal by-product. Fraction 18 was colourless. The column can be washed with 100% acetonitrile, for re-use.

Product "B" (1 g) was separated by a similar method except that the product was dissolved initially in 100% acetonitrile and the filtrate applied to a 2 cm. column packed with 100 g. of the solid phase. Excellent separation of the product was achieved with the aqueous ammonium acetate/acetonitrile eluant.

Although, in this Example, the reverse phase column was used in addition to a conventional column, it is clear that the conventional column achieved little separation of the bis-steroidal by-product and it is intended to omit the conventional column in future preparations.

TEST RESULTS

(a) Preparation of Testicular Material

Human testes were obtained from previously untreated patients undergoing orchidectomy for prostatic cancer. The testes were decapsulated and stored in liquid nitrogen until use. A microsomal preparation was prepared essentially as described by S. E. Barrie et al., J. Steroid Biochem. 6, 1191-5, (1989). The material was then thawed, finely chopped, and homogenised in 0.25M sucrose (5 ml/g wet weight) using a Potter homogeniser. The homogenate was centrifuged at 12000 g for 30 min, and then the microsomes were pelleted by spinning the supernatant at 100,000 g for 1 hr. The pellet was washed by being resuspended in 0.25M sucrose and repelleted. The microsomal pellet was then resuspended in 50 mM sodium phosphate pH 7.4/ glycerol (3/1 v/v) and stored in aliquots in liquid nitrogen.

(b) Determination of 17α-Hydroxylase

The basic assay mixture was EDTA (0.2 mM), dithiothreitol (DTT; 0.1 mM), NADPH (0.25 mM), glucose 6-phosphate dehydrogenase (G6PDH; 6.25 μg/ml), $MgCl_2$ (1 mM), glucose 6-phosphate (G6P; 10 mM) and the substrate, $^3H$-progesterone (3 μM) in sodium phosphate (50 mm), pH 7.4. The compounds under test were dissolved in 50% DMSO and the final concentrations of ethanol and DMSO were 1% each. The assay reaction was carried out for 1 hour and was terminated by the addition of 2 vols. of methanol-acetonitrile (2:1) containing approx. 100 μM unlabelled progesterone, 17α-hydroxyprogesterone, androstenedione, testosterone, and 16α-hydroxyprogesterone. The last-mentioned steroid was added as it appeared that the human enzyme was capable of 16α-hydroxylation as well as 17α-hydroxylation.

The separation of the steroids by HPLC was carried out using an "Uptight" guard column packed with 40–63 μm Nucleosil C18 and a 10 cm main column packed with 5 μm Nucleosil C18 and 60% methanol as eluant. The radioactivity in the peaks of interest was monitored on-line by mixing the HPLC effluent 1:1 with Ecoscint A (National Diagnostics) scintillation fluid, containing 25% acetonitrile, and passing the mixture through a Berthold LB506C radiochemical monitor. The hydroxylase activity was measured as the production of 17α-hydroxyprogesterone, androstenedione and testosterone.

(c) Determination of $C_{17}$–$C_{20}$ Lyase

The mixture was the same as described above for the 17α-hydroxylase except that the substrate was $^3H$-17α-hydroxy- progesterone. The reaction was carried out for 1–2 h. and was stopped by the addition of 2 vols. of methanol/ acetonitrile (2/1 containing approx. 100 μM 17α-hydroxyprogesterone, androstenedione and testosterone.

The HPLC separation used for the lyase involved a mini-re-column "Uptight Guard Column" packed with PELL-ODS (pellicular octadecyl silica) and a 10 cm. main column "Apex C18" column packed with 5 μ, APEX-CAT silica.

The eluant was 38:12:50 methanol:acetonitrile:water flowing at 1 ml/min. The effluent was mixed 1:1 with Ecoscint A containing 5% methanol and 5% acetonitrile and the radioactivity was measured directly by a Berthold LB506C radiochemical detector. The lyase activity was measured as the production of androstenedione and testosterone.

(d) Calculation of $IC_{50}$.

The enzyme activity was measured in the presence of at least 4 concentrations of each compound. The data were for the 4-pyridyl and 2-picolyl compounds of Table 1 fitted by linear regression to the Dixon equation (M. Dixon, E. C. Webb, Enzymes, 2nd ed., Academic Press, New York, 1964). Data for all the other compounds were fitted by non-linear regression to the median effect equation of Chou, J. Theoret. Biol. 39, 253–276 (1976). The correlation coefficients were greater than 0.95 except for the compound of Example 1, where it was 0.91. All the assays were carried out with approx. 4 nM enzyme (as calculated from kinetic measurements) except those for Ketoconazole and the 2- and 4-pyridyl and 2-picolyl compounds of Table 1, in which 25 nM lyase and 10 nM hydroxylase were used. The $IC_{50}$ values are dependent on enzyme concentration when the inhibitor binds tightly (all the compounds tested except the 4-pyridyl and 2-picolyl). Results are shown in Table 2 below.

TABLE 2

(a) Confirmation that variations in the A and B rings of compounds of the invention have little effect on inhibition of hydroxylase and lyase.

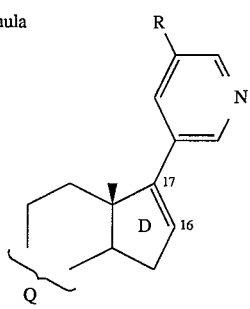

Compounds tested are of formula (3) wherein R = H:

| Q | | $IC_{50}$ (μM) | |
|---|---|---|---|
| | | Lyase | Hydroxylase |
| (structure AcO-) | (Ex. 1) | 0.0097 | 0.0130 |
| (structure HO-) | (Ex. 2) | 0.0029 | 0.0040 |
| (structure) | (Ex. 3) | 0.0056 | 0.0125 |
| (structure O=) | (Ex. 4) | 0.0021 | 0.0028 |
| (structure HO-) | (Ex. 6) | 0.0018 | 0.0026 |
| (structure HO-) | (Ex. 8) | 0.0025 | 0.0043 |
| (structure O=) | (Ex. 9) | 0.0030 | 0.0047 |
| (structure O=, F) | (Ex. 12) | 0.0022 | 0.0033 |
| (structure O=, F) | (Ex. 13) | 0.0032 | 0.0053 |

(b) Confirmation that variation in the C ring of compounds of the invention has little effect on the inhibition of hydroxylase and lyase.

| Compound Tested | $IC_{50}$ (μM) | |
|---|---|---|
| | Lyase | Hydroxylase |
| (Ex. 10) | 0.0025 | 0.0091 |

The comparative $IC_{50}$ figures for Ketoconazole are 0.026 against lyase and 0.065 against hydroxylase.

Assay of Aromatase Activity

Aromatase activity was determined by the method of A. B. Foster et all., J. Med. Chem. 26, 50–54 (1983), using human placental microsomes. For the microsomes used, the Michaelis constant $K_m$ for [1β-$^3$H]androstenedione was 0.039 μM.

The compounds having a pregnenolone-like skeleton in the A and B rings, i.e. 3β-acetoxy- 17-(3-pyridyl)androsta-5,16-diene and its 3-alcohol of Examples 1 and 2, had $IC_{50} > 20$ μM. The compound having a progesterone-like skeleton in the A and B rings, i.e. 17-(3-pyridyl)-androsta-4,16-dien-3-one of Example 4 exhibited also aromatase inhibitory activity with $IC_{50} = 1$ μM.

In Vivo Organ Weight and Endocrine Test in Mice

Male HWT mice, 12 weeks old, were treated daily for 2 weeks, with 5 animals per treatment group. The test compounds were the compound of Examples 1 and 4 (as representative of compounds of the invention having the pregenolone-like and progesterone-like skeletons respectively). Ketoconazole was also tested at three different doses. The test compounds were made up in 5% benzyl alcohol, 95% safflower oil, and were given i.p.. In addition to an untreated control group of animals, there was also a solvent control group which received the same volume of liquid as the test group (5 ml/kg) but no test compound. All animals were sacrificed 24 hours after the last injection. Blood was collected by cardiac puncture into heparinized tubes, and the plasma used for RIA (radio immunoassay) of testosterone and luteinising hormone. The following organs were removed and weighed: adrenals, prostate, seminal vesicles, testes, kidneys. There was no significant body weight loss in any group of mice during the experiments.

Post mortem examination of the mice revealed oil/white deposits i.p. in those treated with compound of Ex. 1 and white deposits throughout the abdomen in those treated with compound of Ex. 4. In all these mice, all organs looked normal. In Ketoconazole-treated animals, adhesions were found in 2/5,2/5,4/5 of the low/middle/top dose groups. The gut and peritoneal wall seemed to be stuck to the seminal vesicles. The livers were brown in the middle/top dose groups.

The weights of organs found in the animals post mortem are shown in Table 3 below. The reductions in weight of all of the prostate, seminal vesicles, testes and kidneys were much greater for the test compounds of the invention than for Ketoconazole. Ketoconazole caused an increase in adrenal weight at the two highest doses, whereas the compounds of the invention had no significant effect, suggesting that they did not inhibit corticosterone biosynthesis.

TABLE 3

| Dose | Mean weight (mg.) ± standard error. | | | | |
|---|---|---|---|---|---|
| | Adrenals | Prostate | Seminal Vesicles | Testes | Kidneys |
| Compound of Ex. 1. | | | | | |
| Controls | 4.5 ± 0.1 | 10.1 ± 0.7 | 189 ± 9 | 146 ± 3 | 709 ± 17 |
| Solvent controls | 4.5 ± 0.4 | 10.2 ± 1.3 | 171 ± 6 | 122 ± 7 | 615 ± 28 |
| 0.02 mmol/kg/day | 4.3 ± 0.2 | 8.0 ± 0.6 | 136 ± 4 | 134 ± 4 | 604 ± 24 |
| 0.1 mmol/kg/day | 4.0 ± 0.2 | 5.3 ± 0.3 | 51 ± 6 | 95 ± 3 | 500 ± 8 |
| 0.5 mmol/kg/day | 4.7 ± 0.2 | 5.6 ± 0.6 | 25 ± 2 | 56 ± 2 | 449 ± 12 |
| Compound of Ex 4. | | | | | |
| Controls | 4.3 ± 0.4 | 8.4 ± 0.2 | 165 ± 18 | 142 ± 8 | 652 ± 45 |
| Solvent controls | 4.4 ± 0.0 | 9.2 ± 0.9 | 152 ± 9 | 122 ± 8 | 589 ± 24 |
| 0.02 mmol/kg/day | 4.7 ± 0.2 | 5.9 ± 0.8 | 108 ± 4 | 117 ± 9 | 599 ± 29 |
| 0.1 mmol/kg/day | 4.6 ± 0.4 | 6.4 ± 0.5 | 61 ± 9 | 105 ± 5 | 549 ± 28 |
| 0.5 mmol/kg/day | 4.9 ± 0.1 | 4.1 ± 0.5 | 25 ± 1 | 59 ± 2 | 468 ± 15 |
| Ketoconazole | | | | | |
| Controls | 4.2 ± 0.2 | 8.9 ± 0.8 | 193 ± 8 | 145 ± 4 | 670 ± 12 |
| Solvent controls | 4.7 ± 0.4 | 9.3 ± 1.2 | 198 ± 18 | 146 ± 3 | 615 ± 25 |
| 0.01 mmol/kg/day | 4.8 ± 0.2 | 9.1 ± 0.8 | 235 ± 18 | 141 ± 5 | 637 ± 22 |
| 0.225 mmol/kg/day | 6.1 ± 0.3 | 10.8 ± 1.4 | 171 ± 5 | 127 ± 7 | 574 ± 23 |
| 0.5 mmol/kg/day | 6.9 ± 0.3 | 9.3 ± 0.9 | 179 ± 20 | 133 ± 6 | 710 ± 30 |

The results indicate the inhibition by the components of the invention of androgen and particularly testosterone synthesis. They are confirmed by endocrinological results shown in Table 4.

Although the solvent itself produced marked depression of testosterone levels, probably due to stress on the animals, the further decrease resulting from the administration of test compounds was much more marked for the compounds of the invention than for ketoconazole. The rise in LH levels is ascribed to a feedback mechanism associated with depletion of testosterone.

TABLE 4

| Endocrinological Results (Mean ± standard error) | | |
| --- | --- | --- |
| | Testosterone nM | LH ng/ml |
| Compound of Ex. 1 | | |
| Controls | 9.8 ± 5.6 | 0.63 ± 0.16 |
| Solvent Controls | 2.5 ± 1.2 | 0.80 ± 0.09 |
| 0.02 Mmol/Kg/Day | 2.7 ± 0.5 | 3.4 ± 0.5 |
| 0.1 Mmol/Kg/Day | 0.2 ± 0.1 | 2.55 ± 0.45 |
| 0.5 Mmol/Kg/Day | 0.1 ± 0.0 | 2.25 ± 0.67 |
| Compound of Ex. 4 | | |
| Control | 27.8 ± 11.4 | Not determined |
| Solvent Control | 11.0 ± 5.6 | " |
| 0.02 Mmol/Kg/Day | 4.5 ± 0.3 | " |
| 0.1 Mmol/Kg/Day | 3.5 ± 1.0 | " |
| 0.5 Mmol/Kg/Day | 0.4 ± 0.1 | " |
| Ketoconazole | | |
| Controls | 17.3 ± 7.1 | 0.66 ± 0.05 |
| Solvent Controls | 1.3 ± 0.4 | 0.25 ± 0.13 |
| 0.1 Mmol/Kg/Day | 0.9 ± 0.2 | 0.39 ± 0.14 |
| 0.225 Mmol/Kg/Day | 0.7 ± 0.1 | 0.75 ± 0.02 |
| 0.5 Mmol/Kg/Day | 0.4 ± 0.1 | 0.76 ± 0.03 |

We claim:

1. A method of preparing a 3β]-hydroxy- or 3β- (lower acyloxy) 16,17-ene-17-(3-pyridyl)-substituted steroid, wherein the 3β-(lower acyloxy) group of steroid has from 2 to 4 carbon atoms, which comprises:
cross-coupling a 3β-hydroxy-16,17-ene-17-iodo or -bromo steroid with a (3-pyridyl)-substituted borane using a palladium complex catalyst, wherein the pyridine ring in said borane is unsubstituted or substituted at the 5-position by an alkyl group of 1 to 4 carbon atoms, in a proportion of at least 1.0 equivalent of borane per equivalent of steroid, in an organic liquid which is a solvent for the 3β-hydroxy steroidal reaction product, and,
where the 3β-(lower acyloxy) ester is to be prepared, reacting the resulting 3β-hydroxy steroidal reaction product with an esterifying agent effective to replace the hydroxy group by a said lower acyloxy group,
wherein (a) the reaction is carried out with 1.0 to 1.2 equivalents of borane per equivalent of steroid or (b) the product of the cross-coupling reaction is crystallized from a mixture of acetonitrile and methanol.

2. A method according to claim 1, wherein the 3β-hydroxy steroidal reaction product, with or without isolation, is reacted with an acetyl-esterifying agent to give the corresponding 3β-acetoxy- 16,17-ene-17-(3-pyridyl) steroid.

3. A method according to claim 1, wherein the starting steroid has a D-ring of the following partial formula

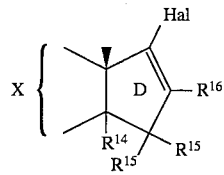

wherein Hal is I or Br, X represents the residue of the A, B and C rings of the steroid, the A ring being substituted by a 3β-hydroxy group, $R^{14}$ represents a hydrogen atom, a halogen atom or an alkyl group of 1 to 4 carbon atoms, each of the $R^{15}$ substituents independently represents a hydrogen atom or an alkyl or alkoxy group of 1 to 4 carbon atoms, a hydroxy group or an alkylcarbonyloxy group of 2 to 5 carbon atoms or together represent an oxo or methylene group or $R^{14}$ and one of the $R^{15}$ groups together represent a double bond and the other $R^{15}$ group represents a hydrogen atom or an alkyl group of 1 to 4 carbon atoms, and $R^{16}$ represents a hydrogen atom, halogen atom, or an alkyl group of 1 to 4 carbon atoms.

4. A method according to claim 3, wherein the starting steroid is 3β-hydroxyandrost-5-en-17 one.

5. A method according to claim 3, wherein the (3-pyridyl)-substituted borane is of formula:

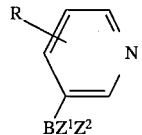

wherein R represents a hydrogen atom or an alkyl group of 1–4 carbon atoms and $Z^1$ and $Z^2$ independently represent hydroxy or alkoxy or alkyl of 1–3 carbon atoms each or $Z^1$ and $Z^2$ together represent an alkylenedioxy group of 2 or 3 carbon atoms.

6. A method according to claim 1, in which the cross-coupling reaction is carried out in two phases, one of which is aqueous and the other of which comprises the said organic liquid.

7. A method according to claim 1, wherein feature (b) of claim 26 is employed and the volumetric ratio of acetonitrile to methanol is at least 5:1.

8. A method according to claim 1, wherein feature (a) of claim 26 is employed and the proportion of borane per equivalent of steroid is from 1.2:1 to 1.5:1.

9. A method according to claim 1, wherein the ester is prepared and after esterification the product is subjected to reverse phase chromatography.

* * * * *